United States Patent [19]

Sasaki et al.

[11] 4,370,279

[45] * Jan. 25, 1983

[54] PROCESS FOR PRODUCTION OF ACRYLONITRILE

[75] Inventors: Yutaka Sasaki, Yokohama; Tomio Nakamura, Ichikawa; Yoshimi Nakamura, Kawasaki; Kiyoshi Moriya, Kanagawa; Hiroshi Utsumi, Yokohama; Shigeru Saito, Tokorozawa, all of Japan

[73] Assignee: Nitto Chemical Industry Co., Ltd., Tokyo, Japan

[*] Notice: The portion of the term of this patent subsequent to Oct. 26, 1993, has been disclaimed.

[21] Appl. No.: 941,351

[22] Filed: Sep. 11, 1978

Related U.S. Application Data

[63] Continuation of Ser. No. 786,740, Apr. 11, 1977, abandoned.

[30] Foreign Application Priority Data

Apr. 10, 1976 [JP] Japan .................................. 51-39813

[51] Int. Cl.³ .......................................... C07C 120/14
[52] U.S. Cl. ................................................ 260/465.3
[58] Field of Search ................................. 260/465.3

[56] References Cited

U.S. PATENT DOCUMENTS 3,668,147  6/1972  Yoshino et al. ................. 252/439 X
3,716,496  2/1973  Yoshino et al. ............. 260/465.3 X
3,988,359  10/1976 Saito et al. ...................... 260/465.3

Primary Examiner—Joseph P. Brust
Attorney, Agent, or Firm—Sughrue, Mion, Zinn, Macpeak & Seas

[57] ABSTRACT

A process for producing acrylonitrile by the vapor-phase catalytic ammoxidation of propylene, which comprises (I) reacting propylene, a molecular oxygen-containing gas and ammonia in the presence of a catalyst expressed by the following empirical formula $$Fe_a Sb_b Mo_c Me_d Te_e Q_f Na_g O_h \cdot (SiO)_i$$

wherein Me is at least one element selected from the group consisting of V and W, Q is at least one element selected from the group consisting of Cu, Mg, Zn and Ni, and the subscripts a, b, c, d, e, f, g, h and i each represents atomic ratios such that when $a=10$; $b=13$ to 28; $c=0.1$ to 2.5; $d=0.05$ to 1; $e=0.2$ to 5; $f=0$ to 4 (in which case $b=13$ to 20), or $f=2$ to 6 (in which case $b=20$ to 28); $g=0$ to 3; $h=$ the number of oxygens corresponding to the oxide formed by the combination of the components, and $i=25$ to 200;

in a fluidized bed catalytic reaction zone at a temperature of about 380 to about 500° C. and a pressure of about 0.2 to about 3 kg/cm²-G while adjusting the propylene/oxygen/ammonia molar ratio to about 1:about 1:about 0.8 to about 1:about 4:about 3;

(II) the catalyst being prepared by

(1) intimately mixing starting materials for the Fe, Mo, Me, Te and Q components in a form soluble in water or nitric acid, a starting material for the Sb component, and silica sol which may or may not contain an Na component, thereby to form a slurry containing these components and having a non-volatile solids content of about 10 to about 50% by weight;

(2) so that the composition of the final catalyst is within the range expressed by the empirical formula above;

(3) spray-drying the resulting slurry, and (4) calcining the resulting spray-dried particles at a temperature of about 600 to about 950° C. thereby to form a catalyst with a composition within the above empirical formula and with all of the Mo, Me, and Te components substantially dissolved in an iron/antimony oxide compound (FeSbO₄) in the form of a solid solution.

34 Claims, 3 Drawing Figures

FIG. 1
CATALYST 4

FIG. 2
CATALYST 17

FIG. 3
CATALYST 24

PROCESS FOR PRODUCTION OF ACRYLONITRILE

This application is a Continuation application of Ser. No. 786,740, filed Apr. 11, 1977, now abandoned.

BACKGROUND OF THE INVENTION

1. Field of the Invention

This invention relates to a process for producing acrylonitrile by a vapor-phase catalytic ammoxidation of propylene. More specifically, the invention relates to a process for producing acrylonitrile by the vapor-phase catalytic ammoxidation of propylene using a silica-supported multi-promoted iron/antimony oxide fluidized catalyst.

2. Description of the Prior Art

Since acrylonitrile is currently produced in very large quantities by the vapor-phase catalytic ammoxidation of propylene, even a slight increase in the yield of acrylonitrile results in a large economical advantage. Continuing efforts have therefore been made to develop catalysts having superior performance for the production of acrylonitrile. In view of recent concerns on environmental problems, development of catalysts which can be used to produce acrylonitrile in high yields with reduced amounts of byproducts, difficult to dispose of, has been strongly desired.

A large number of catalysts useful for the production of acrylonitrile by the vapor-phase catalytic ammoxidation of propylene are known, and many patents have been issued on these catalysts. However, only a few of them show superior results feasible for commercial operations.

An iron/antimony oxide mixed catalyst useful in the vapor-phase catalytic ammoxidation of propylene is disclosed in Japanese Patent Publication No. 19111/1963 (Japanese Pat. No. 420,264), U.S. Pat. No. 3,197,419, and British Pat. No. 983,755. Moreover, improved results are obtained by the addition of particular additives to such a catalyst, as disclosed in U.S. Pat. Nos. 3,338,952, 3,542,843, 3,591,620, 3,668,147, 3,716,496, and 3,988,359. These catalysts, however, are not entirely satisfactory from the standpoint of the yield of acrylonitrile and other properties when a fluidized bed catalytic reactor, which is advantageous in the commercial production of acrylonitrile, is used. In particular, the catalyst disclosed in U.S. Pat. No. 3,988,359 has many advantages, but the strength of this catalyst is not satisfactory for use in a fluidized bed.

SUMMARY OF THE INVENTION

Continued investigations on the catalysts disclosed in U.S. Pat. Nos. 3,668,147, 3,716,496, and 3,988,359 have been made in order to achieve further improvements. These investigations have led to the discovery that the catalytic activities of the catalysts described in these patents are further increased and they have superior strength suitable for use in a fluidized bed catalytic reactor by using Mo and at least one of V and W as an Me component, selecting four kinds of metallic components as a stick-inhibiting component, selecting silica as a carrier component and limiting the amount of Na component carried over mainly from silica sol to below a certain value, restricting the composition of the catalyst to a very narrow range, and producing the catalyst by the method to be described hereinbelow.

Thus, an object of this invention is to provide a process for producing acrylonitrile by the vapor-phase catalytic ammoxidation of propylene, which can be used to produce acrylonitrile in high yields, maintain high acrylonitrile yields over long periods of time even when the molar ratio of oxygen to propylene is low, produce acrylonitrile in high yields even when the molar ratio of ammonia to propylene is low, and maintain high acrylonitrile yields under elevated pressures, and enable the loss of catalyst to be extremely reduced. This object is achieved by using a multi-promoted iron/antimony oxide fluidized catalyst of a composition within a narrow range and of a specified catalyst structure, which comprises an oxide of iron, an oxide of antimony, an oxide of molybdenum, an oxide of at least one metal selected from the group consisting of V and W, an oxide of tellurium, an oxide of at least one metal selected from the group consisting of Cu, Mg, Zn and Ni, and silica.

The present invention provides a process for producing acrylonitrile by the vapor-phase catalytic ammoxidation of propylene, in the presence of a catalyst in which Mo, Me and Te components are dissolved in an iron/antimony oxide compound ($FeSbO_4$) to form a solid solution, with the catalyst being prepared by (1) intimately mixing starting materials for the Fe, Mo, Me, Te and Q components in a form soluble in water or nitric acid, a starting material for the Sb component, and silica sol containing or not containing any Na component, thereby to form a slurry containing these components and having a non-volatile solids content of about 10 to about 50% by weight, (2) so that the composition of the resulting catalyst is within the range expressed by the following empirical formula $$Fe_aSb_bMo_cMe_dTe_eQ_fNa_gO_h\cdot(SiO_2)_i$$

wherein Me is at least one element selected from the group consisting of V and M, Q is at least one element selected from the group consisting of Cu, Mg, Zn and Ni, and subscripts a, b, c, d, e, f, g, h and i each represents the atomic ratios of the indicated components such that when a=10; b=13 to 28; c=0.1 to 2.5; d=0.05 to 1; e=0.2 to 5; f=0 to 4 (in which case b=13 to 20), or f=2 to 6 (in which case b=20 to 28), g=0 to 3, h=the number of oxygens corresponding to an oxide formed by the combination of the components, and i=25 to 200, (3) spray-drying the slurry, and (4) calcining the resulting particles at a temperature in the range of about 600° to about 95° C.

DETAILED DESCRIPTION OF THE INVENTION

It is important that catalysts used in catalytic reactors with a fluidized bed, which is advantageous for the commercial production of acrylonitrile, should be capable of producing acrylonitrile in good yields, permit a moderate rate of reaction, have sufficiently high strength, and undergo little changes in activity and properties in long-term use. Accordingly, it is important to select the composition of the catalyst and establish a method for catalyst preparation, so that the resulting catalyst will meet these requirements.

A catalyst comprising an iron/antimony oxide only as an active ingredient is essentially weak in a reducing atmosphere. Ammoxidation in a low oxygen concentration using this catalyst results in reduced acrylonitrile yields, and in an extreme case, the catalyst is permanently degenerated. U.S. Pat. No. 3,668,147 discloses that the catalytic activity in low oxygen concentrations can be maintained by adding an oxide of at least one metal selected from the group consisting of V, Mo and W. Furthermore, U.S. Pat. No. 3,988,359 discloses that as a result of adding this metal oxide, high acrylonitrile yields can be maintained even when the partial pressure of ammonia is low (that is, even when the molar ratio of ammonia to propylene is decreased).

However, on further investigations, it was ascertained that the operations and effects of V, Mo and W differ from one another in minute details. Specifically, it was found (i) the Mo and V components have a greater effect of inhibiting catalyst degradation in an atmosphere containing a low oxygen concentration than the W component;

(ii) the Mo and V components have a greater effect of inhibiting the decrease of the acrylonitrile yield at a low ammonia/propylene molar ratio than the W component;

(iii) these three components exhibit greater effects (i) and (ii) the larger the amount thereof added, but the Mo component provides higher acrylonitrile yields over a broader range of amounts of the Mo component added than the V and W components;

(iv) the decrease of the acrylonitrile yield caused by an increase in the reaction pressure is of a lower degree when the Mo component is used than when the V and W components are used; and (v) the effects of the Mo component on the rate of reaction are lower than those of the V and W components.

Although it had long been known that the smaller the amounts of these three components added, the easier it is to form a solid solution at the time of finally calcining the catalyst, it was made clear that the catalyst has a higher strength with smaller amounts of these three components.

Based on the information obtained, an Mo component was used in conjunction with at least one of V and W components. As a result, the effects of addition are not reduced even if the total amount of the three components is decreased, and rather, within a specified range, the effects of the addition can be enhanced. Therefore, a catalyst which has sufficiently high attrition resistance to withstand commercial use as a fluidized catalysts has been successfully developed, and moreover, the catalyst is easy to produce.

It has also been found that since the Mo component, whose effect on the rate of reaction is small, is always present in the catalyst used in the present invention, and since the amount of the V and W components, whose effects on the rate of reaction are greater, are decreased, the rate of reaction can be easily adjusted so that such is moderate, and that this capability is exceedingly effective.

If it is desired to provide a sufficient rate of reaction by adding only an Mo component, the amount of the Mo component should be increased, and difficulties will occur. For example, the yield of acrylonitrile and the strength of the catalyst are reduced, and because of a susceptibility to sintering, the final calcination conditions are difficult to select. These difficulties can also be eliminated by using the Mo component in conjunction with at least one of the V and W components.

Iron and antimony components which are basic components of the catalyst used in this invention are selected such that the atomic ratio of the antimony component to the iron component is 13 to 28 (preferably 15 to 25):10.

If the amount of the antimony compound is above the upper limit specified above, a slow rate of reaction results, and the catalyst has insufficient strength as a fluidized catalyst. Even if the catalyst has sufficiently high initial strength, the strength gradually decreases as it is used over long periods of time in the synthesis of acrylonitrile. Furthermore, since, as disclosed in U.S. Pat. No. 3,716,496, sticks consisting of free antimony oxide tend to be formed at the time of the final calcination of the catalyst, a stick-inhibiting component needs to be added in large quantities, in which case the activity of the catalyst is likely to decrease. On the other hand, when the amount of the antimony component is below the lower limit specified above, the yield of acrylonitrile decreases.

Not only are the molar ratios of the iron component to the antimony component important, but also it is important for these components to be present as an iron/antimony oxide compound ($FeSbO_4$).

As stated hereinabove, the Mo and Me components, the latter being at least one of V and W, are used in combination in the catalyst used in the present invention.

The amount of the molybdenum component is selected within a narrow range expressed by an Mo/Fe atomic ratio of 0.1 to 2.5 (preferably 0.1 to 1.5):10. If the molybdenum component is added in an amount larger than the upper limit of this range, the strength of the catalyst is reduced, and it is difficult to form a solid solution at the time of the final calcination of the catalyst. On the other hand, if the amount of the molybdenum component is lower than the lower limit of this range, the high activity of the catalyst obtained cannot be maintained at a low oxygen/propylene molar ratio and a low ammonia/propylene molar ratio and under increased reaction pressures.

The amount of the Me component is selected within a narrow range expressed by an Me/Fe atomic ratio of 0.05 to 1 (preferably 0.05 to 0.7):10. When the Me component is added in an amount larger than the upper limit of this range, the strength of the catalyst is reduced, and it is difficult to control the rate of reaction and also to form a solid solution at the time of the final calcination of the catalyst. On the other hand, if the amount is below the lower limit of this range, the high activity of the catalyst cannot be maintained at a low oxygen/propylene molar ratio and a low ammonia/propylene molar ratio.

As a result of using the Mo component together with at least one of V and W, the amounts of these components required for them to fully exhibit the above-described effects can be decreased as compared with the case of using the Mo, V and W components individually. It is especially preferred therefore that, in terms of atomic ratio, 0.5 to 1.2 of the (Mo+Me) component be added to 10 of the iron component.

U.S. Pat. No. 3,668,147 states that the inclusion of a tellurium component can result in an increase in acrylonitrile selectivity. In the catalyst used in this invention, the effect of the tellurium component is the same as that described in U.S. Pat. No. 3,668,147. The amount of the tellurium component, however, is related to the amounts of the molybdenum component and the Me component. In the catalyst used in this invention, the amount of the tellurium component is selected within a range expressed by a Te/Fe atomic ratio of 0.2 to 5 (preferably 0.5 to 4):10. If the Te component is added in an amount larger than the upper limit of this range, the rate of reaction is low, and the catalyst is not commercially feasible. On the other hand, if the amount of the Te component is below the lower limit described above, the acrylonitrile selectivity is decreased.

When the antimony content is higher than the iron content in iron/antimony oxide catalysts, sticks (minute spiniferous materials formed on the surface of catalyst as projections) composed of free antimony oxide (mainly antimony tetroxide) are frequently formed in the step of calcination performed at high temperatures so as to impart the desired activity to the catalyst. The sticks separate from the catalyst during use, scatter as tacky minute fragments and may cause difficulties in blocking pipings, for example. The formation of such sticks can be prevented by adding a metallic component which reacts with antimony oxide during the calcination of the catalyst without impairing the activity of the catalyst, as disclosed in U.S. Pat. No. 3,716,496.

In the catalyst used in this invention, as well, at least one metallic component selected from the group consisting of Cu, Mg, Zn and Ni is added as component Q. The effect of this metallic component Q in inhibiting stick formation is the same as that disclosed in U.S. Pat. No. 3,716,496. The limitation of the Q component to the four metals described above is due to the fact that they sufficiently inhibit stick formation and tend to increase the yield of acrylonitrile rather than to the mere fact that they have sufficient effect of preventing stick formation without impairing catalytic activity. Furthermore, by selecting the amount of the stick-inhibiting component, both the rate of reaction and the proportions of various by-products can be controlled suitably.

The amount of the component Q added to the catalyst used in this invention varies depending on the ratio between the iron and antimony components. The reason for this will be understandable from the fact that since the sticks consist mainly of antimony tetroxide as stated hereinabove, stick formation occurs only when the Sb/Fe atomic ratio in the catalyst is high, and that stick formation tends to occur to a greater extent as this ratio becomes higher.

Thus, when the Sb/Fe atomic ratio in the catalyst is 13 to 20:10, the Q component is added in an amount expressed by a Q/Fe atomic ratio of 0 to 4 (preferably 0 to 3):10. When the Sb/Fe atomic ratio is 20 to 28:10, the Q component is added in a Q/Fe atomic ratio of 2 to 6 (preferably 2 to 5):10. The ranges of the amount of Q component added partly overlap each other. This is because even when the Sb/Fe atomic ratio is the same, sticks tend to be formed at high calcination temperatures, and the optimum calcination temperature for the catalyst varies depending on changes in the amounts of the Mo, Me and Te added.

U.S. Pat. No. 3,716,496 states that when the Sb component is present in an amount of less than 20 per 10 of the iron component, in terms of atomic ratio, there is very little likelihood of stick formation even in the absence of the Q component, and therefore, it is not necessary to add a stick inhibitor. However, since the Q component used in the present invention has additional effects such as increasing the acrylonitrile yield, controlling the rate of reaction, and controlling the proportions of various by-products formed, the addition of a small amount of the Q component frequently gives rise to good results even when the Sb/Fe atomic ratio is less than 20:10 (except when the amount of antimony is particularly small).

If the amount of the Q component is larger than the upper limit of the above-mentioned range, the yield of acrylonitrile is reduced. If the antimony component is present in an amount of 20 to 28 per 10 of the iron component, in terms of atomic ratio, and the amount of the Q component is below the lower limit specified above, satisfactory inhibition of stick formation is not achieved.

Silica is used as a carrier component in the catalyst used in this invention, because it is superior to other carrier components with regard to the strength of the fluidized catalyst, because it scarcely reacts with the active ingredients of the catalyst (alumina, for example, tends to react with the antimony component), and because it does not adversely affect the activity of the catalyst. Use of silica imparts a strength feasible as a fluidized catalyst, and provides a moderate particle density for achieving a good fluidized condition.

The amount of silica is selected within a range expressed by a silica/iron atomic ratio of 25 to 200 (preferably 40 to 150):10. If the silica is used in an amount larger than the upper limit of this range, the active ingredients of the catalyst are diluted, and sufficient catalytic activity is not exhibited. Moreover, the particle density decreases to increase losses of the catalyst due to scattering. On the other hand, amounts below the lower limit increase the particle density too much and thus reduce the fluidizability of the catalyst. Reduced fluidizability results in decreased acrylonitrile yields.

Silica sol is used as a starting material for the silica. Since silica sol is usually produced from sodium silicate, it tends to contain a sodium component. Furthermore, a small amount of sodium is sometimes added to stabilize the sol. Care much be taken when a silica sol containing sodium is used. The same care must also be taken as to the inclusion of sodium in the starting materials for the other ingredients. The reason is that if sodium is present in an amount larger than a certain critical value in the catalyst used in the present invention, the yield of acrylonitrile decreases.

Some molybdenum/bismuth/iron catalysts for production of acrylonitrile require the presence of a certain amount of alkali metals (for example, those described in U.S. Pat. No. 3,766,092, and Japanese Patent Applications (OPI) Nos. 47476/73 and 129519/75). In the catalyst used in the present invention, sodium is not an active ingredient, but is rather considered to be a detrimental component. No clear reason is presently known for this difference, but it is presumed that the catalyst used in this invention is rather basic compared with molybdenum/bismuth/iron catalysts, and the presence of sodium increases the basicity of the catalyst excessively.

The amount of the sodium component allowable in the catalyst of the invention is less than 3, preferably less than 1.5, per 10 of iron, in terms of atomic ratio. It is not necessary to remove sodium completely from the silica sol at additional expense. For practical purposes, the sodium component can be present preferably in an amount of 0.05 to 1.5 per 10 of iron, in terms of atomic ratio.

U.S. Pat. No. 3,988,359 describes in detail that the iron/antimony oxide should be present as an iron/antimony oxide compound (FeSbO$_4$) in order for it to act effectively as a catalyst for the ammoxidation of propylene and also widely as a catalyst for the oxidation and the oxidative dehydrogenation of olefins; and that in order for a multi-promoted iron oxide/antimony oxide catalyst having at least one component selected from V, Mo and W, Te and Q added thereto to act effectively as a catalyst for the ammoxidation of propylene, the V, Mo, W and Te components should be dissolved in the iron/antimony oxide compound (FeSbO$_4$) to form a solid solution.

Just as is the case in U.S. Pat. No. 3,988,359, in the catalyst used in this invention, the Mo, Me (i.e., V and/or W) and Te should be dissolved in the iron/antimony oxide compound (FeSbO$_4$) to form a solid solution. When the above-described components are present as separate oxides, they scarcely contribute to the function of the catalyst in many cases. Especially when the Mo and Me are present in the free state, the yield of acrylonitrile evidently decreases.

Accordingly, the catalyst used in this invention should be prepared by selecting starting materials and preparing a slurry of the starting materials in the manner to be described hereinbelow.

Starting Materials for the Catalyst

For the Fe, Mo, Me, Te and Q components, starting materials soluble in water or nitric acid are used. A starting material having high reactivity is used for the Sb component.

Starting materials which can be used to provide the iron component in the catalyst are, for example, iron salts of inorganic acids such as iron nitrate or iron chloride, and iron salts of organic acids such as iron acetate or iron oxalate. Iron hydroxide can also be used, and metallic iron, preferably electrolytic iron powder may be used by dissolving such in heated nitric acid. Since it is important for any starting material for iron to be intimately mixed with the other components, it should be in a form soluble in water or nitric acid.

Suitable starting materials for the antimony component include, for example, antimony trioxide, antimony tetroxide, and antimony pentoxide. Substances which will finally become a stable oxide of antimony after chemical treatment, calcination treatment, etc. can also be used. For instance, various antimony hydroxides, and a product obtained by oxidizing metallic antimony with nitric acid can be used. Also, easily hydrolyzable antimony salts, for example, antimony halides such as antimony trichloride or antimony pentachloride can be used. Hydrous oxides obtained by hydrolyzing these antimony halides can also be used.

Examples of suitable starting materials for the molybdenum component are ammonium molybdate, molybdic acid, and a solution of molybdenum trioxide in aqueous ammonia.

Ammonium metavanadate and vanadyl oxalate can be cited as suitable starting materials for the vanadium component. A solution of vanadium pentoxide in aqueous hydrogen peroxide can also be used.

Examples of suitable starting materials for the tungsten component are ammonium tungstate and tungstic acid.

Starting materials for the tellurium component which are suitable are, for example, tellurous acid, telluric acid, and tellurium dioxide. A solution of metallic tellurium or tellurium oxide in nitric acid can also be used.

Starting materials which can be used to furnish the Q component, i.e., the copper, magnesium, zinc and nickel components, are preferably nitrates of these components. A solution of each metallic component, an oxide, thereof or a hydroxide thereof in nitric acid can also be used.

As stated hereinabove, silica sol is used as a starting material for the silica used as a carrier component. Silica sol can be produced using many conventional methods such as acid decomposition or electrolytic dialysis of sodium silicate, hydrolysis of methyl silicate, peptization of silica gel, or ion exchange of sodium silicate. Conveniently, commercially available silica sols can be suitably employed. Many kinds of commercially available silica sols are known, and care must be taken as to their sodium content as described hereinabove. Since many of the commercially available silica sols are prepared from sodium silicate, they tend to contain sodium. The starting silica sol should therefore be selected such that the sodium content of the final catalyst is less than 3, preferably less than 1.5, per 10 of the iron component, in terms of atomic ratio. Preferred examples of silica sols are those which have a silica concentration of about 5 to about 90% by weight, preferably about 10 to about 60% by weight, a silica particle diameter of about 5 to about 100 m$\mu$, and an SiO$_2$/Na$_2$O weight ratio of at least about 30. Silica sols having the same sodium content may result in an increase in the amount of sodium included in the catalyst as the silica content of the catalyst is increased, and care must be taken in this regard.

Preparation of the Starting Material Slurry

In the catalyst used in this invention, the Mo, Me and Te components must be dissolved in the iron/antimony oxide compound to form a solid solution. It is necessary, therefore, for the slurry prepared from the above-described starting materials for the catalyst ingredients to be highly uniform. Needless to say, the individual materials should be fully mixed in the slurry thus prepared, and as good a dispersion of these ingredients as possible should be maintained. The order of adding these starting materials is not critical, and may be determined optionally in view primarily of the ease of operation.

Use of the method disclosed in U.S. Pat. Nos. 3,657,155 and 3,686,138 provides advantageous results in enhancing the strength of the catalyst. This method involves adjusting the pH of the slurry containing the above-described materials to not more than about 7 (preferably about 1 to about 4) e.g., by adding an alkali such as ammonia or an acid such as nitric acid while thoroughly mixing the slurry, and then heat-treating the slurry at a temperature of about 40° to about 150° C. (preferably about 80° to about 100° C.) for at least 20 minutes (preferably about 1 to about 12 hours) while maintaining a slurry form. When such a treatment of the slurry is performed, it is necessary for at least a part of each of the Fe and Sb materials and silica sol to be present in the slurry prior to pH adjustment (when a trivalent antimony compound is used as a starting material for the Sb component, it is necessary for nitrate ion to be present also). The Mo, Me, Te and Q materials may be mixed initially, or may be mixed after the heat-treatment of the slurry.

In order to increase the strength of the catalyst, it is also preferred to employ a method in which the prepared slurry is spray-dried, calcined and pulverized, and the resulting powder is mixed with silica sol to prepare a slurry again. Specifically, this method comprises intimately mixing the starting materials for the Fe, Mo, Me, Te, Q and Sb components and a part of the silica sol to prepare a slurry, then spray-drying the slurry prepared, calcining the resulting particles at a temperature within the range of about 600° to about 950° C., then pulverizing the resulting calcined particles to a fine powder, and mixing the remainder of the silica sol with the resulting powder to form a slurry again.

Spray-Drying the Slurry

The slurry thus prepared is then spray-dried to form fine spherical particles. Any known spray-drying method can be used as desired. Various spray-drying devices such as a high-pressure nozzle type device, a rotary disc-type device, or a two fluid nozzle-type device can be used. The concentration of the slurry to be spray-dried is about 10 to about 50% by weight calculated on the basis of the oxides of the elements forming the catalyst (non-volatile solids content). Although this range is not critical, concentrations below the lower limit of this range are economically disadvantageous, and concentrations above the upper limit of this range are inconvenient in handling the slurry.

Spray-drying is carried out under appropriately controlled conditions with appropriately adjusted slurry concentrations so that the desired particle size distribution can be obtained. Generally, in spray-drying a suitable gas inlet temperature can range from about 200° to about 400° C. and an average residence time is on the order of several seconds. Suitably, a moisture level of less than 10% by weight in the spray-dried particles is obtained. Calcination sometimes may cause some change in the particle size distribution obtained, but usually there is not very much change. Accordingly, the particle size distribution of the final catalyst can be adjusted by appropriately choosing the spray-drying conditions.

Calcination of the Catalyst

The fine particulate catalyst after spray-drying is calcined to impart a high degree of activity to the catalyst. The calcination conditions are important in the activation of the catalyst. The optimal calcination conditions vary depending on the composition of the catalyst and the method of catalyst preparation, but the particulate catalyst is finally calcined at a temperature in the range of about 600° to about 950° C. Preferably, the spray-dried catalyst is calcined at a temperature of about 200° to about 600° C. for about 1 to about 50 hours, and then finally at about 600° to about 950° C. for about 1 to about 50 hours. The atmosphere in which calcination is performed is preferably non-reducing e.g., in an atmosphere such as air, a mixture of an inert gas such as nitrogen and argon, etc.. It is preferred to perform the calcination in a stream of air.

Many types of calcining devices, such as a tunnel furnace, a rotary furnace or a fluidization furnace, can be used. For commercial operations, a rotary furnace and a fluidization furnace are preferred. Since the final calcination is carried out at high temperatures, the use of a fluidization furnace in which the temperature distribution is good and where caking of the catalyst does not occur during calcination is preferred. For example, the fluidizing calcination can be carried out by the method disclosed in Japanese Patent Publication No. 3756/75 in which calcination is carried out in a fluidized bed device containing a catalyst in the fluidized bed portion with a ratio of the cross-sectional area of the upper surface to that of the bottom being 1.2 to 3, setting the bottom as a standard, while maintaining the apparent linear velocity in a column of a fluidizing gas at not less than 15 cm/sec. at the bottom and at not more than 60 cm/sec. at the upper surface.

In the present invention, propylene used is not limited to substantially pure propylene, but may be a mixture of propylene with a paraffinic hydrocarbon such as ethane, propane or butane. When a mixture of propylene with other materials is used a suitable concentration is about 50% by volume propylene.

In the present invention, oxygen may be employed in any form, but for economic reasons, air is preferred. Air may be used diluted with an inert gas with the inert gas being present in an amount of about 21% by volume to about 70% by volume, or as suitably enriched with oxygen, as desired.

Generally, the partial pressure of propylene is sometimes increased in the production of acrylonitrile in order to increase productivity. In such a case, the acrylonitrile selectivity usually decreases. The catalyst used in this invention, however, reduces the degree of decrease in acrylonitrile selectivity. This gives rise to the advantage that the process of the present invention can be performed under increased partial pressures of propylene (caused by a decrease in the partial pressure of nitrogen) by using air enriched with oxygen.

The oxygen/propylene molar ratio in the feedstock supplied to the reactor in the present invention is within a range of from about 1:1 to about 4:1. A suitable oxygen concentration fed is about 10 to about 30% by volume of the feed. Since the catalyst used in this invention provides a high acrylonitrile selectivity, relatively low oxygen/propylene molar ratios, i.e. from about 1.5:1 to about 2.5:1, suffice. By reducing the oxygen/propylene molar ratio, namely by decreasing the amount of air used, the output (space time yield) of acrylonitrile per unit time per unit volume of the reactor, namely productivity, can be greatly increased. In addition to providing high acrylonitrile selectivity, the catalyst used in this invention has superior catalytic activity even when the partial pressure of oxygen is low.

The ammonia/propylene molar ratio in the feedstock supplied to the reactor can be varied within a range of from about 0.8:1 to about 3:1, preferably from about 0.9:1 to about 1.5:1. The catalyst used in this invention might cause the oxidative decomposition (i.e., burning) of ammonia in the absence of propylene (i.e., in the presence of ammonia and air alone). However, in the copresence of propylene, namely under actual ammoxidation reaction conditions, there is no substantial burning of ammonia. Moreover, this catalyst does not increase the amounts of by-products as is the case with conventional catalysts even if the ratio of ammonia fed decreases. In this case, only the amount of HCN formed somewhat decreases and acrolein is formed in a tiny amount, but the formation of acrylic acid is not observed. Accordingly, there is substantially no significance in using ammonia in excess. Thus, it is especially preferred that the ammonia/propylene molar ratio in the feed-stock supplied to the reactor be from about 0.9:1 to about 1.15:1.

By decreasing the ratio of ammonia fed, the amount of unreacted ammonia which flows out from the reactor and remains in the reacted gaseous product can be decreased. Consequently, the amount of acid (usually sulfuric acid) to be consumed for neutralizing ammonia in the effluent gas can be reduced. This further results in the advantage that the amount of ammonium salts (usually ammonium sulfate) contained in the waste water from acrylonitrile manufacturing facilities can be reduced, and the treatment of the waste water is facilitated. Accordingly, in addition to providing high acrylonitrile selectivity, the catalyst used in this invention has superior catalytic activity even when the partial pressure of ammonia is low.

Since the catalyst used in the invention does not cause a burning of ammonia, the amount of oxygen consumed is small in this regar also, and therefore, the oxygen/propylene molar ratio and the oxygen/ammonia molar ratio in the feedstock can be reduced, thus providing the advantage of greatly increasing productivity. Burning of ammonia tends to form nitrogen oxide ($NO_x$) which causes a serious problem of atmospheric pollution. The catalyst of the invention, which does not cause a burning of ammonia is quite free from this problem.

In the vapor-phase catalytic oxidation and the ammoxidation reaction, it has been the frequent practice to feed water into the reaction system in order to increase the selectivity of the desired product (to further inhibit a burning of ammonia in the case of the ammoxidation reaction). There are many examples in which water is added also in the ammoxidation of propylene. In the present invention, however, there is scarcely any need for water addition which is disadvantageous both from an energy and operational standpoint, since the catalyst used does not cause a burning of ammonia and, even in the absence of water, a sufficiently high acrylonitrile selectivity can be maintained. However, water may be added as needed because at times the addition of a minor amount of water has an effect of somewhat inhibiting the formation of by-products, especially gaseous carbon dioxide. In such a case, a sufficient amount of water is not more than 2 moles per mole of propylene fed.

The composition of the feed gas described hereinabove is with regard to the total sum of gases entering the reactor. The feed gas may be passed incrementally to the reactor.

In the present invention, a suitable reaction temperature is within a range of about 380° to about 500° C., preferably within a range of about 400° to about 480° C.

A suitable reaction pressure is within a range of about 0.2 to about 3 kg/cm$^2$-G, preferably within a range of about 0.3 to about 1.5 kg/cm$^2$-G. In the production of acrylonitrile by an ammoxidation reaction, elevated reaction pressures tend to reduce acrylonitrile yields. In spite of this, the reaction is usually carried out at somewhat high pressure because of the economical advantage that the output of acrylonitrile per unit volume of reactor (space time yield) increase. With the catalyst used in this invention, too, elevated reaction pressures tend to reduce acrylonitrile yields to some extent, but the degree of reduction is smaller than with conventional catalysts. Thus, the catalyst in accordance with this invention is also improved in this respect.

A suitable apparent contact time is within a range of about 1 to about 30 seconds, preferably within a range of about 2 to about 20 seconds.

Even when catalysts have superior performance at an early stage in their use, they are not superior commercial catalysts unless their performance lasts over long periods of time under economical reaction conditions. The catalyst used in this invention is superior in this respect, too, and retains its high performance over long periods of time under severe reaction conditions.

The process of this invention is performed using a fluidized bed catalytic reactor. Commercial-scale production of acrylonitrile is performed using a fixed bed catalytic reactor and a fluidized bed catalytic reactor. The latter type of reactor has many advantages, and has gained widespread acceptance. For example, with this type of reactor the reaction temperature can be maintained uniform, heat removed easily, the concentration of the starting gas, increased and a large size can be easily built.

Since the catalyst in accordance with this invention is used in a fluidized bed catalytic reactor, the particle size distribution and strength of the catalyst are important.

A suitable particle size distribution is such that catalyst particles having a size within a range of about 20 to about 200 microns account for at least about 80% by weight of the entire particles. If the amount of very fine particles is excessively large, increasing losses of catalyst during operation occur. On the other hand, when the proportions of large particles is too high the fluidized condition of the catalyst at the time of reaction becomes poor, and the results of reaction are unsatisfactory.

Catalysts having low strength cannot be commercially used even if good acrylonitrile yields are achieved. This is because the unit production cost assigned to the catalyst increases to raise the cost of acrylonitrile.

The catalyst used in this invention has a high performance and a high strength even when used over long periods of time under reaction conditions which are advantageous for commercial production of acrylonitrile.

The reaction product can be recovered by any desired method known in the art. For example, the effluent gas from the reactor is washed with cold water or with a solvent suitable for the extraction of acrylonitrile to separate HCN and acetonitrile as well as the desired acrylonitrile, followed by further separation and recovery of the desired acrylonitrile.

The following Examples and Comparative Examples are given to specifically illustrate embodiments and advantages of the present invention.

The yield and selectivity of the product as used herein are defined as shown below.

$$\text{Conversion of Propylene (\%)} \ (= \text{yield of the product}) = \frac{\text{Weight of Carbon in the Product}}{\text{Weight of Carbon in Propylene Fed}} \times 100$$

$$\text{Selectivity (\%)} = \frac{\text{Weight of Carbon in the Product}}{\text{Weight of Carbon in Propylene Reacted}} \times 100$$

Catalyst Preparation

Catalysts Nos. 1 to 14 are in accordance with this invention, and Catalysts Nos. 15 to 24 are comparison catalysts for demonstrating the significance of the present invention.

In preparation of the catalysts, three kinds of silica sol shown in Table 1 were used. In Table 2, the silica sols used are designated as A, B or C according to the descriptions in Table 1.

TABLE 1

| Silica Sols Description | | | |
|---|---|---|---|
| | Silica Sol | | |
| | A | B | C |
| SiO$_2$ Concentration (% by weight) | 20 | 30 | 30 |
| SiO$_2$/Na$_2$O Weight Ratio | 666.7 | 107.1 | 46.2 |

The catalysts were prepared as follows:

Catalyst 1

A catalyst having the empirical formula Fe$_{10}$Sb$_{1.5}$Mo$_{0.3}$W$_{0.2}$Te$_{0.5}$Na$_{0.15}$O$_{47.6}$(SiO$_2$)$_{50}$ was prepared using the following procedure.

Powdery antimony trioxide (1.749 kg) was employed. (I)

Electrolytic iron powder (0.447 kg) was employed. Water (2 liters) and 3.2 liters of nitric acid (specific gravity 1.38) were mixed and heated. The iron powder was added incrementally to the mixture to dissolve the iron. (II)

Ammonium paramolybdate (42.3 g) and 43.2 g of ammonium paratungstate were dissolved in 500 ml of water. Furthermore, 91.9 g of telluric acid (H$_6$TeO$_6$) was added and dissolved. (III)

12.0 Kg of silica sol (silica concentration: 20% by weight; particle size: 10–20 mμ; Na$_2$O content: 0.03% by weight) was employed. (IV)

(III), (II), and (I) were added in this order to (IV), and with good stirring, 15% aqueous ammonia was added incrementally to adjust the pH to 2. The slurry was heated at 100° C. for 8 hours with good stirring. The concentration of the slurry was adjusted to about 20% by weight (calculated as the oxides), and the slurry was spray-dried in a conventional manner using a rotary disc-type spray-drying apparatus.

The resulting fine spherical particles were calcined at 250° C. for 8 hours, and at 400° C. for 16 hours in an externally heated rotary furnace, and finally calcined at 790° C. for 4 hours in a fluidizing calcination furnace externally heated with an electric heater while fludizing the catalyst with air.

The final catalyst obtained had an average particle size of 63 microns, and contained 6% of particles with a size of 20 microns or less and 100% of particles with a size of 149 microns or less.

Catalyst 2

A catalyst having the empirical formula Fe$_{10}$Sb$_{1.8}$Mo$_{0.5}$V$_{0.2}$Te$_{1.2}$Na$_{0.15}$O$_{55.6}$(SiO$_2$)$_{50}$ was prepared in the same way as in the preparation of Catalyst 1 except that ammonium metavanadate was used instead of the ammonium paratungstate and the final calcination was carried out at 770° C. for 4 hours.

Catalyst 3

A catalyst having the empirical formula Fe$_{10}$Sb$_{2.0}$Mo$_{0.5}$W$_{0.5}$Te$_{1.5}$Cu$_1$Ni$_3$Na$_{0.09}$O$_{64.1}$(SiO$_2$)$_{30}$ was prepared in the same way as in the preparation of Catalyst 1 except that nitrates were used as the starting materials for the copper and nickel components; these nitrates were dissolved in a predetermined amount of pure water and added to a solution of iron nitrate; and the final calcination was performed at 760° C. for 4 hours.

Catalyst 4

Figure 1:
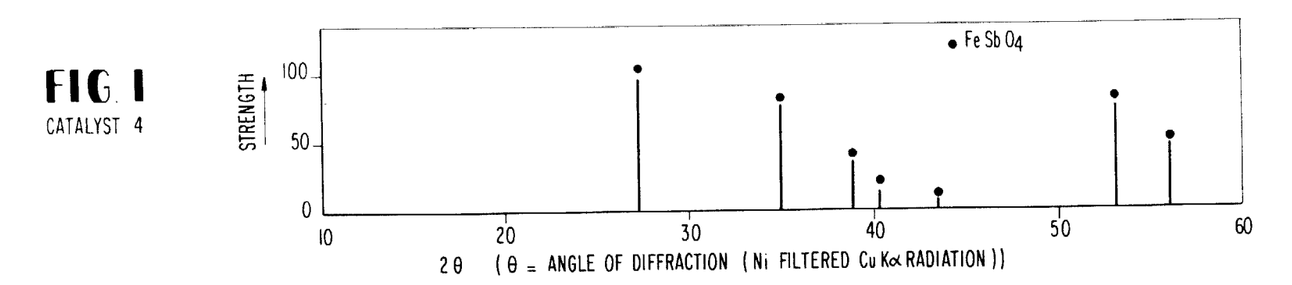
FIGS. 1 to 3 are X-ray diffraction patterns of catalysts prepared in accordance with this invention and catalysts for comparison as described in the Examples herein.

A catalyst having the empirical formula Fe$_{10}$Sb$_{2.0}$Mo$_{0.8}$W$_{0.2}$Te$_{1.7}$Cu$_{2.5}$Na$_{0.15}$O$_{64.0}$(SiO$_2$)$_{50}$ was prepared in the same way as in the preparation of Catalyst 1 except that copper nitrate was used as a starting material for the copper component, and was mixed and dissolved in a solution of iron nitrate, and the final calcination was carried out at 740° C. for 4 hours. The X-ray diffraction pattern of this catalyst is shown in FIG. 1.

Catalyst 5

A catalyst having the empirical formula Fe$_{10}$Sb$_{2.0}$Mo$_{1.0}$V$_{0.2}$Te$_{2.5}$Cu$_3$Na$_{0.23}$O$_{66.6}$(SiO$_2$)$_{80}$ was prepared in the same way as in the preparation of Catalyst 2 except that copper nitrate was used as the starting material for the copper component, and dissolved in a predetermined amount of pure water and added to the slurry which had been heat-treated; and the final calcination was carried out at 750° C. for 4 hours in an electrically heated box-type furnace.

Catalyst 6

A catalyst having the empirical formula Fe$_{10}$Sb$_{2.0}$Mo$_{0.8}$V$_{0.1}$Te$_{2.0}$Cu$_{2.5}$Na$_{0.23}$O$_{65.3}$(SiO$_2$)$_{80}$ was prepared in the same way as in the preparation of Catalyst 5 except that metallic tellurium powder was used as the starting material for the tellurium component; it was added to and dissolved in a solution of electrolytic iron powder; and the final calcination was carried out at 750° C. for 5 hours.

Catalyst 7

A catalyst having the empirical formula Fe$_{10}$Sb$_{2.0}$Mo$_{0.5}$V$_{0.1}$W$_{0.3}$Te$_{2.3}$Cu$_3$Na$_{0.29}$O$_{65.4}$(SiO$_2$)$_{100}$ was prepared in the same way as in the preparation of Catalyst 1 except that antimony pentoxide hydrate prepared from antimony pentachloride was used as the starting material for the antimony component; vanadyl oxalate was used as the starting material for the vanadium component; copper nitrate was used as the starting material for the copper component; and the final calcination was carried out at 770° C. for 5 hours.

Catalyst 8

A catalyst having the empirical formula Fe$_{10}$Sb$_{2.0}$Mo$_{0.1}$V$_{0.1}$W$_{0.6}$Te$_{1.5}$Zn$_2$Na$_{0.23}$O$_{62.5}$(SiO$_2$)$_{80}$ was prepared in the same way as in the preparation of Catalyst 1 except that ammonium metavanadate was used as the starting material for the vanadium component; zinc nitrate was used as the starting material for the zinc component; and the final calcination was carried out at 760° C. for 4 hours.

Catalyst 9

A catalyst having the empirical formula Fe$_{10}$Sb$_{2.0}$Mo$_{0.5}$V$_{0.3}$Te$_{2.0}$Cu$_2$Mg$_2$Na$_{1.45}$O$_{66.0}$(SiO$_2$)$_{80}$ was prepared in the same way as in the preparation of Catalyst 5 except that magnesium hydroxide, dissolved in nitric acid, was used as the starting material for the magnesium component, and the final calcination was carried out at 780° C. for 4 hours in a box-type furnace heated electrically.

Catalyst 10

A catalyst having the empirical formula $Fe_{10}Sb_{2.0}Mo_{1.0}V_{0.2}W_{0.1}Te_{3.0}Ni_4Na_{0.38}O_{68.5}(SiO_2)_{130}$ was prepared in the same way as in the preparation of Catalyst 1 except that ammonium metavanadate was used as the starting material for the vanadium component; nickel nitrate was used as the starting material for the nickel component; and the final calcination was carried out at 760° C. for 4 hours.

Catalyst 11

A catalyst having the empirical formula $Fe_{10}Sb_{2.5}Mo_2V_{0.06}Te_{3.5}Cu_3Na_{1.09}O_{79.7}(SiO_2)_{60}$ was prepared in the same way as in the preparation of Catalyst 5 except that the final calcination was carried out at 690° C. for 4 hours.

Catalyst 12

A catalyst having the empirical formula $Fe_{10}Sb_{2.5}Mo_{1.0}W_{0.1}Te_{1.5}Cu_4Na_{1.09}O_{75.8}(SiO_2)_{60}$ was prepared in the same way as in the preparation of Catalyst 1 except as noted below. Antimony trichloride was used as the starting material for the antimony component. It was hydrolyzed with aqueous ammonia, and washed well with water. Copper nitrate was used as the starting material for the copper component, and it was mixed and dissolved in a solution of iron nitrate. The final calcination was carried out at 740° C. for 5 hours.

Catalyst 13

A catalyst having the empirical formula $Fe_{10}Sb_{2.5}Mo_{0.3}W_{0.5}Te_{2.0}Mg_4Na_{0.90}O_{75.9}(SiO_2)_{50}$ was prepared in the same way as in the preparation of Catalyst 4 except that antimony pentoxide sol was used as the starting material for the antimony component; magnesium nitrate was used instead of copper nitrate; and the final calcination was carried out at 760° C. for 5 hours.

Catalyst 14

A catalyst having the empirical formula $Fe_{10}Sb_{2.7}Mo_{0.7}V_{0.2}Te_{2.5}Cu_5Na_{0.90}O_{82.1}(SiO_2)_{50}$ was prepared in the following manner.

Metallic antimony powder having a particle size of less than 100 microns (0.974 kg) was employed. Nitric acid (specific gravity: 1.38; 3.5 liters) was heated to about 80° C., and the antimony powder was gradually added to the nitric acid. After the antimony had been completely oxidized, the excess nitric acid was removed. The resulting oxidation product was washed five times with 2 liters of water, and pulverized with a ball mill. (I)

Electrolyzed iron powder (0.447 kg) was employed. Three liters of nitric acid (specific gravity: 1.38) was mixed with 4 liters of water. The mixture was heated to about 80° C. The iron powder was added gradually to this mixture to dissolve the iron powder completely. (II).

Ammonium paramolybdate (98.9 g) was dissolved in 0.5 liter of water. (III)

Ammonium metavanadate (18.7 g) was dissolved in 2 liters of water. (IV)

Telluric acid (459 g) was dissolved in 2.67 kg of silica sol (silica concentration: 30% by weight; particle diameter: 10 to 20 mμ; $Na_2O$ content: 0.28% by weight). (V)

(III), (IV), (II) and (I) were added in this order to (V), and the mixture was stirred well. The resulting slurry was spray-dried.

The resulting fine spherical particles were calcined at 300° C. for 4 hours, and at 650° C. for 4 hours. Pure water (2 liters) was added, and the calcined catalyst particles were wet-pulverized using a vibratory mill to adjust the particle diameter to less than 10 microns. 5.34 kg of the same silica sol as used in (V) above was added and mixed well.

The resulting slurry was spray-dried, and the fine spherical particles obtained were calcined at 200° C. for 4 hours, at 400° C. for 4 hours, and finally at 750° C. for 5 hours. An electrically heated box-type furnace was used in the calcination.

All of Catalysts 1 to 14 exhibited the same X-ray diffraction pattern as Catalyst 4 shown in FIG. 1. The diffraction intensities of these catalysts varied according to the concentrations of the catalyst ingredients and the final calcination temperatures, but the formation of free oxides of Mo, V, W and Te was not observed.

Catalyst 15

A catalyst having the empirical formula $Fe_{10}Sb_{2.5}Mo_{1.0}W_{0.5}Te_3Cu_{0.5}Na_{1.09}O_{76.5}(SiO_2)_{60}$ was prepared in the same way as in the preparation of Catalyst 1 except that copper nitrate was used as the starting material for the copper component, and mixed with and dissolved in a solution of iron nitrate; and the final calcination was carried out at 710° C. for 4 hours. This catalyst had a lower copper content than the catalyst, within the scope of the invention.

Catalyst 16

A catalyst having the empirical formula $Fe_{10}Sb_{3.0}Mo_{1.5}V_{0.1}Te_4Cu_2Ni_2Na_{1.09}O_{90.3}(SiO_2)_{60}$ was prepared in the same way as in the preparation of Catalyst 1 except that ammonium metavanadate was used instead of the ammonium paratungstate; nitrates were used as the starting materials for the copper and nickel components (predetermined amounts of these are dissolved in pure water and added to a solution of iron nitrate); and the final calcination was carried out at 730° C. for 4 hours. This catalyst had a higher antimony content than the catalysts within the scope of the invention.

Catalyst 17

Figure 2:
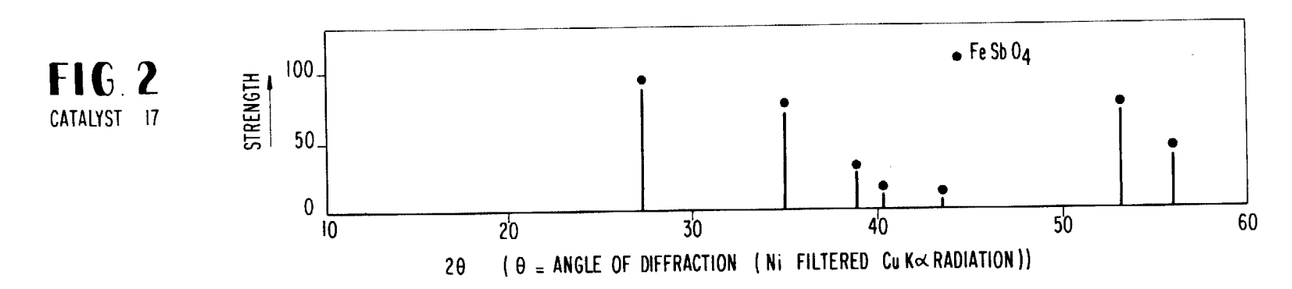

A catalyst having the empirical formula $Fe_{10}Sb_{2.8}Mo_{2.7}V_{0.1}Te_5Cu_{6.5}Na_{0.20}O_{96}(SiO_2)_{70}$ was prepared in the same way as in the preparation of Catalyst 1 except that ammonium metavanadate was used instead of the ammonium paratungstate; copper nitrate was used as the starting material for the copper component and mixed with and dissolved in a solution of iron nitrate; and the final calcination was carried out at 660° C. for 4 hours. This catalyst had a higher molybdenum content than the catalysts within the scope of the invention. The X-ray diffraction pattern of this catalyst is shown in FIG. 2.

Catalyst 18

A catalyst having the emprical formula $Fe_{10}Sb_{2.5}Mo_{1.0}W_{0.1}Te_{1.5}Cu_4Na_{0.06}O_{75.3}(SiO_2)_{20}$ was prepared in the same way as in the preparation of Catalyst 1 except that copper nitrate was used as the starting material for the copper component and mixed with and dissolved in a solution of iron nitrate; and the final calcination was carried out at 690° C. for 5 hours. This catalyst had a lower silica content than the catalysts within the scope of the invention.

Catalyst 19

A catalyst having the empirical formula $Fe_{10}Sb_{20}Mo_{0.2}W_{1.5}Te_{2.5}Ni_3Na_{0.15}O_{68.2}(SiO_2)_{50}$ was prepared in the same way as in the preparation of Catalyst 1 except that nickel nitrate was used as the starting material for the nickel component and mixed with and dissolved in a solution of iron nitrate; and the final calcination was carried out at 750° C. for 4 hours. This catalyst had a higher tungsten content than the catalysts within the scope of the invention.

Catalyst 20

A catalyst having the empirical formula $Fe_{10}Sb_{20}Mo_{0.8}V_{0.1}Te_{2.0}Cu_{2.5}Na_{3.4}O_{65.9}(SiO_2)_{80}$ was prepared in the same way as in the preparation of Catalyst 6 except that Silica Sol C having a high Na content was used as the silicca sol. The catalyst obtained had a higher sodium content than the catalysts within the scope of the invention.

Catalyst 21

A catalyst having the empirical formula $Fe_{10}Sb_{20}Mo_{0.8}W_{0.2}Te_{1.7}Cu_{2.5}Na_{0.61}O_{64.2}(SiO_2)_{210}$ was prepared in the same way as in the preparation of Catalyst 1 except that copper nitrate was used as the starting material for the copper component and mixed with and dissolved in a solution of iron nitrate, and the final calcination was carried out at 770° C. for 4 hours. The resulting catalyst had a higher silica content than the catalysts within the scope of the invention.

Catalyst 22

A catalyst having the emperical formula $Fe_{10}Sb_{2.5}Mo_{1.0}W_{0.1}Te_{1.5}Cu_4Na_{4.1}O_{77.4}(SiO_2)_{60}$ was prepared in the same way as in the preparation of Catalyst 12 except that the product obtained by hydrolyzing antimony trichloride with sodium hydroxide and washing the hydrolyzate with water was used as the starting material for the antimony component, and the final calcination was carried out at 710° C. for 5 hours. Because the water washing of the hydrolyzate of antimony oxide (found to be a Valentinite-type antimony trioxide by X-ray diffraction analysis) was insufficient, the resulting catalyst had a higher Na content than the catalysts within the scope of the invention.

Catalyst 23

A catalyst having the empirical formula $Fe_{10}Sb_{2.5}Mo_{0.25}Te_{1.0}Cu_{0.5}Na_{1.09}O_{68.8}(SiO_2)_{60}$ was prepared in the same way as in the preparation of Catalyst 1 except tht copper nitrate was used as the starting material for the copper component and mixed with and dissolved in a solution of iron nitrate; the ammonium paratungstate was not added; and the final calcination was carried out at 810° C. for 4 hours. The resulting catalyst did not contain an Me component, and was outside the scope of the invention.

Catalyst 24

Figure 3:
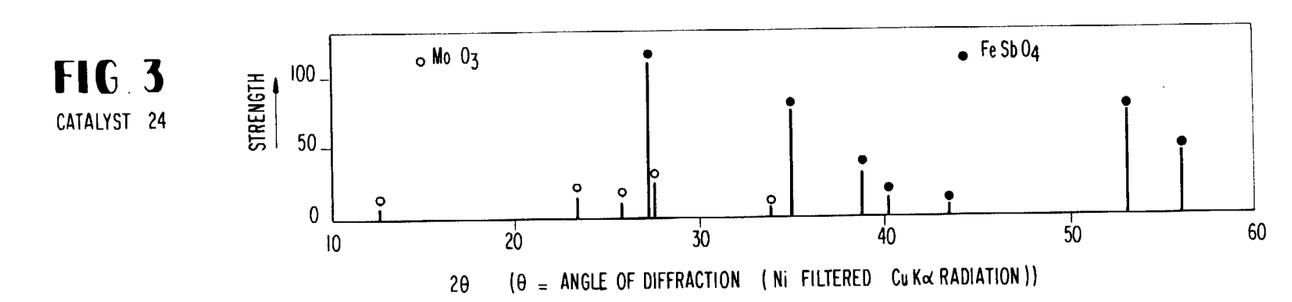

A catalyst having the empirical formula $Fe_{10}Sb_{2.5}Mo_2V_{0.06}Te_{3.5}Cu_3Na_{1.09}O_{81.7}(SiO_2)_{60}$ was prepared in the same way as in the preparation of Catalyst 11 except that molybdenum trioxide was used as a raw material for the molybdenum component, and the final calcination was carried out at 690° C. for 4 hours. In the resulting catalyst, a part of the molybdenum component was present as a free oxide (see FIG. 3). This catalyst had a structure outside the scope of the invention. The X-ray diffraction pattern of this catalyst is shown in FIG. 3.

Catalyst Testing Methods

Each of the catalysts obtained was tested for the following items.

(1) Test for Catalyst Strength

The test was performed by the method described in "Test Methods for Synthetic Cracking Catalysts" (American Cyanamid Company, 6/31-4m-1/57) known as a method for testing fluidized catalytic cracking catalysts (so-called FCC catalysts). The test was performed on particles having a size of 63 to 105 microns.

The attrition rate (%) shown in Table 2 was obtained from the following relationship.

$$\text{Attrition rate (\%)} = R = \frac{B}{C - A} \times 100$$

A: the weight (g) of the catalyst which wore away during a period of 0 to 5 hours B: the weight (g) of the catalyst which wore away during a period of 5 to 15 hours C: the weight (g) of the catalyst used in the test Catalyst having higher strengths have smaller attrition rate (%) (=R value).

(2) Test for Catalyst Activity

Using a fluidized bed reactor including a catalyst fluidizing portion with an inside diameter of 5 cm and a height of 2 meters, a starting gaseous mixture (propylene, ammonia and air) was fed into the reactor so that the apparent linear velocity of the gaseous mixture became 15 cm/sec.

Table 3 shows the results obtained under the following conditions.

Molar ratio of air/propylene fed = 10.5
Molar ratio of ammonia/propylene fed = 1.05

Table 4 shows the results of the activity testing over long periods of time, and Table 5 shows the results of the strength test.

TABLE 2

Catalyst Strength Test Results

| Catalyst | Fe | Sb | Mo | V or W | Te | Q | | Na | Si | Silica Sol | Temperature (°C.) | Time (hr) | Attrition Rate (%) |
|---|---|---|---|---|---|---|---|---|---|---|---|---|---|
| 1 | 10 | 15 | 0.3 | W 0.2 | 0.5 | 0 | | 0.15 | 50 | A | 790 | 4 | 1.1 |
| 2 | 10 | 18 | 0.5 | V 0.2 | 1.2 | 0 | | 0.15 | 50 | A | 770 | 4 | 0.8 |
| 3 | 10 | 20 | 0.5 | W 0.2 | 1.5 | Cu 1 | Ni 3 | 0.09 | 30 | A | 760 | 4 | 1.5 |
| 4 | 10 | 20 | 0.8 | W 0.2 | 1.7 | Cu 2.5 | | 0.15 | 50 | A | 740 | 4 | 0.7 |
| 5 | 10 | 20 | 1.0 | V 0.2 | 2.5 | Cu 3 | | 0.23 | 80 | A | 750 | 4 | 0.8 |

TABLE 2-continued

Catalyst Strength Test Results

| Catalyst | Fe | Sb | Mo | V or W | Te | Q | | Na | Si | Silica Sol | Calcination Temperature (°C.) | Calcination Time (hr) | Attrition Rate (%) |
|---|---|---|---|---|---|---|---|---|---|---|---|---|---|
| 6 | 10 | 20 | 0.8 | V 0.1 | 2.0 | Cu | 2.5 | 0.23 | 80 | A | 750 | 5 | 0.9 |
| 7 | 10 | 20 | 0.5 | V 0.1 W 0.3 | 2.3 | Cu | 3 | 0.29 | 100 | A | 770 | 5 | 1.1 |
| 8 | 10 | 20 | 0.1 | V 0.1 W 0.6 | 1.5 | Zn Cu | 2 2 | 0.23 | 80 | A | 760 | 4 | 0.3 |
| 9 | 10 | 20 | 0.5 | V 0.3 | 2.0 | Mg | 2 | 1.45 | 80 | B | 780 | 4 | 0.5 |
| 10 | 10 | 20 | 1.0 | V 0.2 W 0.1 | 3.0 | Ni | 4 | 0.38 | 130 | A | 760 | 4 | 0.5 |
| 11 | 10 | 25 | 2.0 | V 0.06 | 3.5 | Cu | 3 | 1.09 | 60 | B | 690 | 4 | 1.8 |
| 12 | 10 | 25 | 1.0 | W 0.1 | 1.5 | Cu | 4 | 1.09 | 60 | B | 740 | 5 | 1.3 |
| 13 | 10 | 25 | 0.3 | W 0.5 | 2.0 | Mg | 4 | 0.90 | 50 | B | 760 | 5 | 1.2 |
| 14 | 10 | 27 | 0.7 | V 0.2 | 2.5 | Cu | 5 | 0.90 | 50 | B | 750 | 5 | 1.5 |
| 15 | 10 | 25 | 1.0 | W 0.5 | 3 | Cu | 0.5 | 1.09 | 60 | B | 710 | 4 | 3.4 |
| 16 | 10 | 30 | 1.5 | V 0.1 | 4 | Cu Ni | 2 2 | 1.09 | 60 | B | 730 | 4 | 5.8 |
| 17 | 10 | 28 | 2.7 | V 0.1 | 5 | Cu | 6.5 | 0.20 | 70 | A | 660 | 4 | 16.3 |
| 18 | 10 | 25 | 1.0 | W 0.1 | 1.5 | Cu | 4 | 0.06 | 20 | A | 690 | 5 | 44.2 |
| 19 | 10 | 20 | 0.2 | W 1.5 | 25 | Ni | 3 | 0.15 | 50 | B | 750 | 4 | 1.3 |
| 20 | 10 | 20 | 0.8 | V 0.1 | 2.0 | Cu | 2.5 | 3.4 | 80 | C | 750 | 5 | 0.7 |
| 21 | 10 | 20 | 0.8 | W 0.2 | 1.7 | Cu | 2.5 | 0.61 | 210 | A | 770 | 4 | 1.3 |
| 22 | 10 | 25 | 1.0 | W 0.1 | 1.5 | Cu | 4 | 4.1 | 60 | A | 710 | 5 | 1.1 |
| 23 | 10 | 25 | 0.25 | 0 | 1.0 | Cu | 0.5 | 1.09 | 60 | B | 810 | 4 | 2.1 |
| 24 | 10 | 25 | 2 | V 0.06 | 3.5 | Cu | 3 | 1.09 | 60 | B | 690 | 4 | 2.2 |

TABLE 3

Catalyst Activity Test Results

| Catalyst | Reaction Conditions Pressure (kg/cm²G) | Temperature (°C.) | Contact Time (sec.) | C₃H₆ Conversion (%) AN[1] | CH₃CN | HCN | C₃H₆ Conversion (%) | AN[1] Selectivity (%) |
|---|---|---|---|---|---|---|---|---|
| 1 | 0.3 | 435 | 4.5 | 79.9 | 0.6 | 6.4 | 98.6 | 81.0 |
| 2 | 0.3 | 435 | 4.0 | 81.5 | 0.4 | 5.2 | 97.9 | 83.2 |
| 3 | 0.3 | 430 | 4.0 | 80.8 | 0.5 | 5.8 | 98.1 | 82.4 |
| 4 | 0.5 | 435 | 3.5 | 81.1 | 0.3 | 5.4 | 98.5 | 82.3 |
| 5 | 0.5 | 435 | 3.5 | 81.3 | 0.3 | 5.3 | 98.2 | 82.8 |
| 6 | 0.5 | 430 | 4.0 | 80.9 | 0.4 | 5.5 | 97.6 | 82.9 |
| 7 | 0.5 | 440 | 5.0 | 79.8 | 0.4 | 5.4 | 97.5 | 81.8 |
| 8 | 0.3 | 450 | 3.5 | 79.7 | 0.8 | 6.2 | 98.4 | 81.0 |
| 9 | 0.5 | 430 | 4.5 | 80.3 | 0.7 | 5.6 | 98.6 | 81.4 |
| 10 | 0.3 | 440 | 5.0 | 80.1 | 0.4 | 5.5 | 98.8 | 81.1 |
| 11 | 0.3 | 430 | 3.5 | 80.0 | 0.5 | 5.7 | 97.8 | 81.8 |
| 12 | 0.3 | 440 | 3.0 | 80.5 | 0.5 | 5.2 | 97.9 | 82.2 |
| 13 | 0.3 | 450 | 4.0 | 80.7 | 0.7 | 5.9 | 98.2 | 82.2 |
| 14 | 0.3 | 430 | 4.0 | 80.6 | 0.4 | 5.6 | 98.1 | 82.2 |
| 15 | 0.5 | 430 | 4.5 | 79.5 | 0.5 | 5.1 | 97.8 | 81.3 |
| 16 | 0.5 | 420 | 4.5 | 79.1 | 0.4 | 5.8 | 98.2 | 80.5 |
| 17 | 0.5 | 420 | 5.0 | 78.3 | 1.2 | 5.3 | 98.5 | 80.5 |
| 18[2] (2) | — | — | — | — | — | — | — | — |
| 19 | 0.5 | 410 | 3.5 | 74.6 | 1.3 | 6.7 | 97.1 | 76.8 |
| 20 | 0.5 | 430 | 4.0 | 60.1 | 0.8 | 3.6 | 86.1 | 69.8 |
| 21 | 0.5 | 450 | 6.0 | 70.3 | 0.2 | 4.3 | 87.6 | 80.3 |
| 22 | 0.3 | 430 | 3.5 | 57.3 | 0.6 | 3.4 | 81.1 | 70.7 |
| 23 | 0.5 | 460 | 6.0 | 74.2 | 0.3 | 5.6 | 98.1 | 75.6 |
| 24 | 0.3 | 430 | 3.5 | 70.1 | 0.2 | 5.1 | 96.3 | 72.8 |

[1]AN: Acrylonitrile
[2]No evaluation due to extremely low catalyst strength.

TABLE 4

Long Term Catalyst Activity Test Results

| | Test Conditions Gases fed (molar ratio) | | | Reaction Pressure (kg/cm² · G) | Reaction Temperature (°C.) | Contact Time (sec) | C₃H₆ Conversion (%) | | | | | | Total C₃H₆ Conversion (%) | AN Selectivity (%) |
|---|---|---|---|---|---|---|---|---|---|---|---|---|---|---|
| | C₃H₆ | NH₃ | Air | | | | AN | CH₃ CN | HCN | CO₂ | CO | AL | | |
| Catalyst 4 | | | | | | | | | | | | | | |
| Initial | 1 | 1.03 | 10.2 | 0.5 | 430 | 4.0 | 80.7 | 0.5 | 5.2 | 10.4 | 2.7 | 0.2 | 99.7 | 80.9 |
| 1000 hrs later | 1 | 1.03 | 10.2 | 0.5 | 430 | 4.0 | 80.5 | 0.4 | 5.1 | 10.3 | 2.1 | 0.3 | 98.7 | 81.6 |
| Catalyst 15 | | | | | | | | | | | | | | |
| Initial | 1 | 1.03 | 10.2 | 0.5 | 430 | 4.5 | 79.0 | 0.4 | 5.2 | 10.4 | 2.8 | 0.4 | 98.2 | 80.4 |

TABLE 4-continued

| | | | | | | Long Term Catalyst Activity Test Results | | | | | | | |
|---|---|---|---|---|---|---|---|---|---|---|---|---|---|
| | Test Conditions | | | | | | | | | | | | |
| | Gases fed (molar ratio) | | | Reaction Pressure | Reaction Temperature | Contact Time | $C_3H_6$ Conversion (%) | | | | | | Total $C_3H_6$ Conversion | AN Selectivity |
| | $C_3H_6$ | $NH_3$ | Air | $(kg/cm^2 \cdot G)$ | (°C.) | (sec) | AN | $CH_3$ CN | HCN | $CO_2$ | CO | AL | (%) | (%) |
| 1000 hrs later | 1 | 1.03 | 10.2 | 0.5 | 435 | 4.5 | 78.4 | 0.3 | 5.0 | 10.8 | 3.2 | 0.3 | 98.0 | 80.0 |

AL = Acrolein

TABLE 5

| Long Term Catalyst Activity Test Results | | |
|---|---|---|
| | Attrition Rate (%) | |
| | Before Test | After Test |
| Catalyst 4 | 0.7 | 0.8 |
| Catalyst 15 | 3.4 | 5.5 |

Catalyst 15 had inferior attrition resistance to the catalysts of this invention as can be seen from the results in Table 2, and the strength of Catalyst 15 was reduced further during the long-term test as can be seen from the results in Table 5. It can be seen from the results in Table 2 that Catalysts 16 to 18 had very low attrition resistance. It is further seen that Catalysts 19 to 24 were inferior to the catalysts of this invention in acrylonitrile yields.

The results in Table 2 and 3 demonstrate that Catalysts 1 to 14 in accordance with the present invention are superior fluidized catalysts which provide high acrylonitrile yields and have high attrition resistance.

It is clear from the results in Table 4 and 5 that the catalysts in accordance with the present invention provide high acrylonitrile yields even when the ammonia/propylene molar ratio and the air/propylene molar ratio (i.e., the oxygen/propylene molar ratio) are decreased, and even under these severe conditions, high acrylonitrile yields are maintained and the catalysts have high strength endurable to long-term use.

While the invention has been described in detail and with reference to specific embodiments thereof, it will be apparent to one skilled in the art that various changes and modifications can be made therein without departing from the spirit and scope thereof.

What is claimed is:

1. A process for producing acrylonitrile by the vapor-phase catalytic ammoxidation of propylene, which comprises (I) reacting propylene, a molecular oxygen-containing gas and ammonia in the presence of a catalyst expressed by the following empirical formula $Fe_aSb_bMo_cMe_dTe_eQ_fNa_gO_h \cdot (SiO_2)_i$ wherein Me is at least one element selected from the group consisting of V and W,
Q is at least one element selected from the group consisting of Cu, Mg, Zn and Ni, and
the subscripts a, b, c, d, e, f, g, h and i each represents atomic ratios such that when a=10; b=13 to 20; c=0.1 to 2.5; d=0.05 to 1; e=0.2 to 5; f=0 to 4; g=0 to 3; h=the number of oxygens corresponding to the oxide formed by the combination of said components; and i=25 to 200;
in a fluidized bed catalytic reaction zone at a temperature of about 380° to about 500° C. and a pressure of about 0.2 to about 3 kg/cm²-G while adjusting the propylene/oxygen/ammonia molar ratio to about 1:about 1:about 0.8 to about 1:about 4:about 3;

(II) said catalyst being prepared by (1) intimately mixing starting materials for said Fe, Mo, Me, Te and Q components in a form soluble in water or nitric acid, a starting material for the Sb component, and silica sol, thereby to form a slurry containing these components and having a non-volatile solids content of about 10 to about 50% by weight;

(2) so that the composition of the final catalyst is within the range expressed by said empirical formula above;

(3) spray-drying the resulting slurry, and (4) calcining the resulting spray-dried particles at a temperature of about 600° to 950° C. thereby to form a catalyst with a composition within the above empirical formula and with all of the Mo, Me, and Te components substantially dissolved in an iron/antimony oxide compound ($FeSbO_4$) in the form of a solid solution.

2. The process of claim 1, wherein Q in the catalyst empirical formula is Cu.

3. The process of claim 1, wherein the starting materials for the Fe and Q components are nitrates.

4. The process of claim 1, wherein the starting materials for the Mo and Me components are ammonium salts of the oxyacids thereof.

5. The process of claim 1, wherein the starting material for the Te component is a product obtained by oxidizing metallic tellurium with nitric acid, tellurous acid, or telluric acid.

6. The process of claim 1, wherein the starting material for the Sb component is antimony trioxide or a product obtained by oxidizing metallic antimony with nitric acid.

7. The process of claim 1, wherein the silica sol has a silica particle diameter of about 5 to about 100 mμ, and a silica concentration of about 10 to about 60% by weight.

8. The process of claim 1, wherein the slurry is prepared by intimately mixing starting materials for the Fe, Mo, Me, Te and Q components in a form soluble in water or nitric acid, a starting material for the Sb component, nitrate ion, and silica sol to prepare a slurry containing these components and having a non-volatile solids content of about 10 to about 50% by weight, adjusting the pH of the slurry to not more than about 7, and heat-treating the resulting slurry at a temperature within a range of about 40° to about 150° C. for at least about 20 minutes while maintaining the slurry form; and then spray-drying the slurry.

9. The process of claim 1, wherein the slurry is prepared by first forming a slurry at least containing a starting material for the Fe component in a form soluble in water or nitric acid, a starting material for the Sb component, nitrate ion, and silica sol, adjusting the pH of the slurry to not more than about 7, heat-treating the resulting slurry at a temperature within a range of about 40° to about 150° C. for at least about 20 minutes while maintaining the slurry form, then adding starting materials for the other components in a form soluble in water or nitric acid to the heat-treated slurry and intimately mixing the mixture to form a slurry containing all of the components and having a non-volatile solids content of about 10 to about 50% by weight; and then spray-drying the resulting slurry.

10. The process of claim 1, wherein the spray-dried particles are calcined at about 200° to 600° C. for about 1 to about 50 hours, and then at about 600° to about 950° C. for about 1 to about 50 hours.

11. The process of claim 10, wherein the final calcination is carried out in a fluidized bed calcination furnace.

12. The process of claim 1, wherein the spray-drying is performed such that at least about 80% by weight of the catalyst particles obtained by calcination have a particle size in the range of about 20 to about 200 microns.

13. The process of claim 1, wherein the reaction temperature is within a range of about 400° to about 480° C.

14. The process of claim 1, wherein the reaction pressure is within a range of about 0.3 to about 1.5 kg/cm²-G.

15. The process of claim 1, wherein the propylene/oxygen/ammonia molar ratio in the feed gaseous mixture is about 1:about 1.5:about 0.9 to about 1:about 2.5:about 1.5.

16. The process of claim 1 wherein the starting material for the Sb component is selected from the group consisting of antimony trioxide, antimony tetroxide, antimony pentoxide, substances which will become a stable oxide of antimony after chemical treatment or calcination, a product obtained by oxidizing metallic antimony with nitric acid, easily hydrolyzable antimony salts and hydrous oxides obtained by hydrolyzing antimony halides.

17. The process of claim 16 wherein the substance which will finally become a stable oxide of antimony is an antimony hydroxide and the easily hydrolyzable antimony salt is an antimony halide.

18. A process for producing acrylonitrile by the vapor-phase catalytic ammoxidation of propylene, which comprises
(I) reacting propylene, a molecular oxygen-containing gas and ammonia in the presence of a catalyst expressed by the following empirical formula wherein Me is at least one element selected from the group consisting of V and W,
Q is at least one element selected from the group consisting of Cu, Mg, Zn and Ni, and
the subscripts a, b, c, d, e, f, g, h and i each represents atomic ratios such that when $a=10$; $b=20$ to 28; $c=0.1$ to 2.5; $d=0.05$ to 1; $e=0.2$ to 5; $f=2$ to 6; $g=0$ to 3; $h=$the number of of oxygens corresponding to the oxide formed by the combination of said components; and $i=25$ to 200;
in a fluidized bed catalytic reaction zone at a temperature of about 380° to about 500° C. and a pressure of about 0.2 to about 3 kg/cm²-G while adjusting the propylene/oxygen/ammonia molar ratio to about 1:about 1:about 0.8 to about 1:about 4:about 3;

(II) said catalyst being prepared by
(1) intimately mixing starting materials for said Fe, Mo, Me, Te and Q components in a form soluble in water or nitric acid, a starting material for the Sb component, and silica sol, thereby to form a slurry containing these components and having a non-volatile solids content of about 10 to about 50% by weight;
(2) so that the composition of the final catalyst is within the range expressed by said empirical formula above;
(3) spray-drying the resulting slurry, and
(4) calcining the resulting spray-dried particles at a temperature of about 600° to 950° C. thereby to form a catalyst with a composition within the above empirical formula and with all of the Mo, Me, and Te components substantially dissolved in an iron/antimony oxide compound (FeSbO₄) in the form of a solid solution.

19. The process of claim 18, wherein Q in the catalyst empirical formula is Cu.

20. The process of claim 18, wherein the starting materials for the Fe and Q components are nitrates.

21. The process of claim 18, wherein the starting materials for the Mo and Me components are ammonium salts of the oxyacids thereof.

22. The process of claim 18, wherein the starting material for the Te component is a product obtained by oxidizing metallic tellurium with nitric acid, tellurous acid, or telluric acid.

23. The process of claim 18, wherein the starting material for the Sb component is antimony trioxide or a product obtained by oxidizing metallic antimony with nitric acid.

24. The process of claim 18, wherein the silica sol has a silica particle diameter of about 5 to about 100 mμ, and a silica concentration of about 10 to about 60% by weight.

25. The process of claim 18, wherein the slurry is prepared by intimately mixing starting materials for the Fe, Mo, Me, Te and Q components in a form soluble in water or nitric acid, a starting material for the Sb component, nitrate ion, and silica sol to prepare a slurry containing these components and having a non-volatile solids content of about 10 to about 50% by weight, adjusting the pH of the slurry to not more than about 7, and heat-treating the resulting slurry at a temperature within a range of about 40° to about 150° C. for at least about 20 minutes while maintaining the slurry form; and then spray-drying the slurry.

26. The process of claim 18, wherein the slurry is prepared by first forming a slurry at least containing a starting material for the Fe component in a form soluble in water or nitric acid, a starting material for the Sb component, nitrate ion, and silica sol, adjusting the pH of the slurry to not more than about 7, heat-treating the resulting slurry at a temperature within a range of about 40° to about 150° C. for at least about 20 minutes while maintaining the slurry form, then adding materials for the other components in a form soluble in water or nitric acid to the heat-treated slurry and intimately mixing the mixture to form a slurry containing all of the components and having a non-volatile solids content of about 10 to about 50% by weight; and then spray-drying the resulting slurry.

27. The process of claim 18, wherein the spray-dried particles are calcined at about 200° to 600° C. for about 1 to about 50 hours, and then at about 600° to about 950° C. for about 1 to about 50 hours.

28. The process of claim 18, wherein the final calcination is carried out in a fluidized bed calcination furnace.

29. The process of claim 18, wherein the spray-drying is performed such that at least about 80% by weight of the catalyst particles obtained by calcination have a particle size in the range of about 20 to about 200 microns.

30. The process of claim 18, wherein the reaction temperature is within a range of about 400° to about 480° C.

31. The process of claim 18, wherein the reaction pressure is within a range of about 0.3 to about 1.5 kg/cm²-G.

32. The process of claim 18, wherein the propylene-/oxygen/ammonia molar ratio in the feed gaseous mixture is about 1:about 1.5:about 0.9 to about 1:about 2.5:about 1.5.

33. The process of claim 18 wherein the starting material for the Sb component is selected from the group consisting of antimony trioxide, antimony tetroxide, antimony pentoxide, substances which will become a stable oxide of antimony after chemical treatment or calcination, a product obtained by oxidizing metallic antimony with nitric acid, easily hydrolyzable antimony salts and hydrous oxides obtained by hydrolyzing antimony halides.

34. The process of claim 33 wherein the substances which will finally become a stable oxide of antimony oxide is an antimony hydroxide and the easily hydrolyzable antimony salt is an antimony halide.

* * * * *